(12) United States Patent
Zufi et al.

(10) Patent No.: US 10,791,848 B2
(45) Date of Patent: Oct. 6, 2020

(54) ADAPTIVE SENSORY OUTPUTS SYNCHRONIZED TO INPUT TEMPOS FOR SOOTHING EFFECTS

(71) Applicant: KIDS2, INC., Atlanta, GA (US)

(72) Inventors: Jonathan Zufi, Atlanta, GA (US); Scott Wells, Atlanta, GA (US); Alan Hightower, Austell, GA (US)

(73) Assignee: KIDS2, INC., Atlanta, GA (US)

( * ) Notice: Subject to any disclaimer, the term of this patent is extended or adjusted under 35 U.S.C. 154(b) by 0 days.

(21) Appl. No.: 16/421,856

(22) Filed: May 24, 2019

(65) Prior Publication Data
US 2019/0357697 A1    Nov. 28, 2019

Related U.S. Application Data

(60) Provisional application No. 62/676,113, filed on May 24, 2018.

(51) Int. Cl.
| | |
|---|---|
| *G10H 1/40* | (2006.01) |
| *A47D 13/10* | (2006.01) |
| *A61B 5/024* | (2006.01) |
| *A61B 5/00* | (2006.01) |

(Continued)

(52) U.S. Cl.
CPC ............ *A47D 13/102* (2013.01); *A61B 5/024* (2013.01); *A61B 5/486* (2013.01); *A61M 21/02* (2013.01); *A61M 2021/0027* (2013.01); *A61M 2021/0061* (2013.01); *G10K 2210/3051* (2013.01)

(58) Field of Classification Search
CPC .. G10H 1/40; G10H 1/0008; G10H 2210/076; G10H 2210/391; G10H 2210/341; G10H 2210/375; G10H 2250/311; G10H 2210/371; G10H 2220/086; G10H 2210/071;

(Continued)

(56) References Cited

U.S. PATENT DOCUMENTS

| | | |
|---|---|---|
| 2,259,629 A | 10/1941 | Fisher |
| D290,843 S | 7/1987 | Murphy |
| D345,161 S | 3/1994 | Murphy |

(Continued)

FOREIGN PATENT DOCUMENTS

| | | |
|---|---|---|
| CA | 2503698 A1 | 9/2006 |
| CA | 2728410 A1 | 12/2009 |

(Continued)

OTHER PUBLICATIONS

Invitation to Pay Additional Fees and partial International Search Report for PCT/US2019/033909; dated Sep. 5, 2019; 15 pgs.

*Primary Examiner* — Marlon T Fletcher
(74) *Attorney, Agent, or Firm* — Gardner Groff & Greenwald, PC

(57) ABSTRACT

Sensory outputs are synchronized to input tempos for providing soothing and other effects for children and other persons. In example embodiments, juvenile products such as rockers and swings have motors that are controlled to produce an oscillatory motion with an adaptive tempo that is synchronized to rhythmic inputs such as a parent's heartbeat. In other example embodiments, juvenile products such as music players are controlled to output signals to play songs via speakers with an adaptive tempo that is synchronized to rhythmic inputs such as an infant's respiratory rate.

19 Claims, 6 Drawing Sheets

(51) Int. Cl.
*A61M 21/02* (2006.01)
*A61M 21/00* (2006.01)

(58) Field of Classification Search
CPC ............ A63B 71/0686; A63B 2230/06; A63B 2220/836; A63B 23/185
See application file for complete search history.

(56) References Cited

U.S. PATENT DOCUMENTS

| | | | |
|---|---|---|---|
| 5,803,786 | A | 9/1998 | McCormick |
| 6,116,983 | A | 9/2000 | Long et al. |
| 6,716,031 | B2 | 4/2004 | Wood et al. |
| 7,227,965 | B1 | 6/2007 | Sutton |
| D664,564 | S | 7/2012 | Gillett et al. |
| 8,515,092 | B2 | 8/2013 | Rucker |
| 8,819,533 | B2 | 8/2014 | Trotto et al. |
| 9,510,693 | B2 | 12/2016 | Cordier et al. |
| 9,533,235 | B2 | 1/2017 | Chen |
| 10,258,761 | B2 | 4/2019 | Smudde |
| 10,518,161 | B2 * | 12/2019 | Asukai ................... H03G 3/20 |
| 2006/0107822 | A1 * | 5/2006 | Bowen ................ G10H 1/0008 84/612 |
| 2007/0060446 | A1 * | 3/2007 | Asukai ............... A63B 24/0021 482/8 |
| 2007/0169614 | A1 * | 7/2007 | Sasaki ................ A63B 69/0028 84/612 |
| 2013/0295817 | A1 | 11/2013 | Weber et al. |
| 2015/0179157 | A1 * | 6/2015 | Chon .................... G10H 1/0066 84/645 |
| 2015/0195494 | A1 | 7/2015 | Alvarez |
| 2016/0058201 | A1 * | 3/2016 | Pavkov ................. A47D 13/107 297/440.22 |
| 2016/0372095 | A1 * | 12/2016 | Lyske .................. G10H 1/0025 |
| 2017/0221463 | A1 * | 8/2017 | Lenhert ................ G10H 1/0025 |
| 2018/0166053 | A1 * | 6/2018 | Turner ..................... G10H 1/40 |
| 2019/0357697 | A1 * | 11/2019 | Zufi ...................... A61B 5/024 |

FOREIGN PATENT DOCUMENTS

| | | |
|---|---|---|
| CN | 1070071 A | 3/1993 |
| EP | 0517540 A2 | 12/1992 |
| WO | 2005082472 A1 | 9/2005 |
| WO | 2006085237 A1 | 8/2006 |
| WO | 2007044329 A2 | 4/2007 |
| WO | 2010102083 A1 | 9/2010 |
| WO | 2011100441 A1 | 8/2011 |

* cited by examiner

ADAPTIVE SENSORY OUTPUTS SYNCHRONIZED TO INPUT TEMPOS FOR SOOTHING EFFECTS

CROSS-REFERENCE TO RELATED APPLICATION

This application claims the benefit of U.S. Provisional Patent Application Ser. No. 62/676,113 filed May 24, 2018, the entirety of which is hereby incorporated herein by reference for all purposes.

TECHNICAL FIELD

The present disclosure relates generally to the field of systems and methods for providing sensory experiences for soothing effects, and more particularly to children's products incorporating such systems and methods for soothing children.

BACKGROUND

Various products in markets ranging from infant soothing, to elderly care, and general entertainment are commonly equipped to output preloaded/predefined content, motions, or haptic movements for a soothing or other effect. In the infant care space, such products include rockers, swings, bassinets, play yards, music players, and other juvenile products. The content commonly includes menus of preloaded songs or sounds for outputting via speakers, the motions commonly include preloaded options for rocking motions caused by controlled motors or other motion-imparting devices, and the haptic movements commonly include pulses produced by vibrators or other haptic devices. While these products are of some benefit in providing soothing effects, further advances in this area are desired and would be of greater benefit.

Accordingly, needs exist for improvements in products for children, seniors, and/or others that provide enhanced soothing, comforting, and/or relaxing effects. It is to the provision of solutions meeting these and other needs that the present disclosure is primarily directed.

SUMMARY

The present disclosure is generally directed to devices, systems, and methods for adapting sensory outputs for synchronization to input tempos for providing soothing and/or other effects for children and other persons. In example embodiments, juvenile products such as rockers and swings have motors (or other motion-imparting devices) that are controlled to produce an oscillatory motion with an adaptive tempo that is synchronized to rhythmic inputs such as a parent's heartbeat. In other example embodiments, juvenile products such as music players are controlled to output signals to play songs via speakers with an adaptive tempo that is synchronized to rhythmic inputs such as an infant's respiratory rate.

In other embodiments, these and related adaptive sensory output features are implemented in other product types such as elderly care products and general entertainment and/or relaxation products. For example, a rocking chair can be outfitted to output haptic movements (e.g., for a back massage) or to play music at an adaptive tempo that is synchronized to rhythmic inputs such as the oscillatory tempo at which the chair occupant manually rocks the chair.

These and other aspects, features, and advantages will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments and are not restrictive of the disclosure, as claimed.

DETAILED DESCRIPTION OF EXAMPLE EMBODIMENTS

The present disclosure may be understood more readily by reference to the following detailed description of example embodiments taken in connection with the accompanying drawing figures, which form a part of this disclosure. It is to be understood that this disclosure is not limited to the specific devices, methods, conditions, or parameters described and/or shown herein, and that the terminology used herein is for the purpose of describing particular embodiments by way of example only and is not intended to be limiting of the claims. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
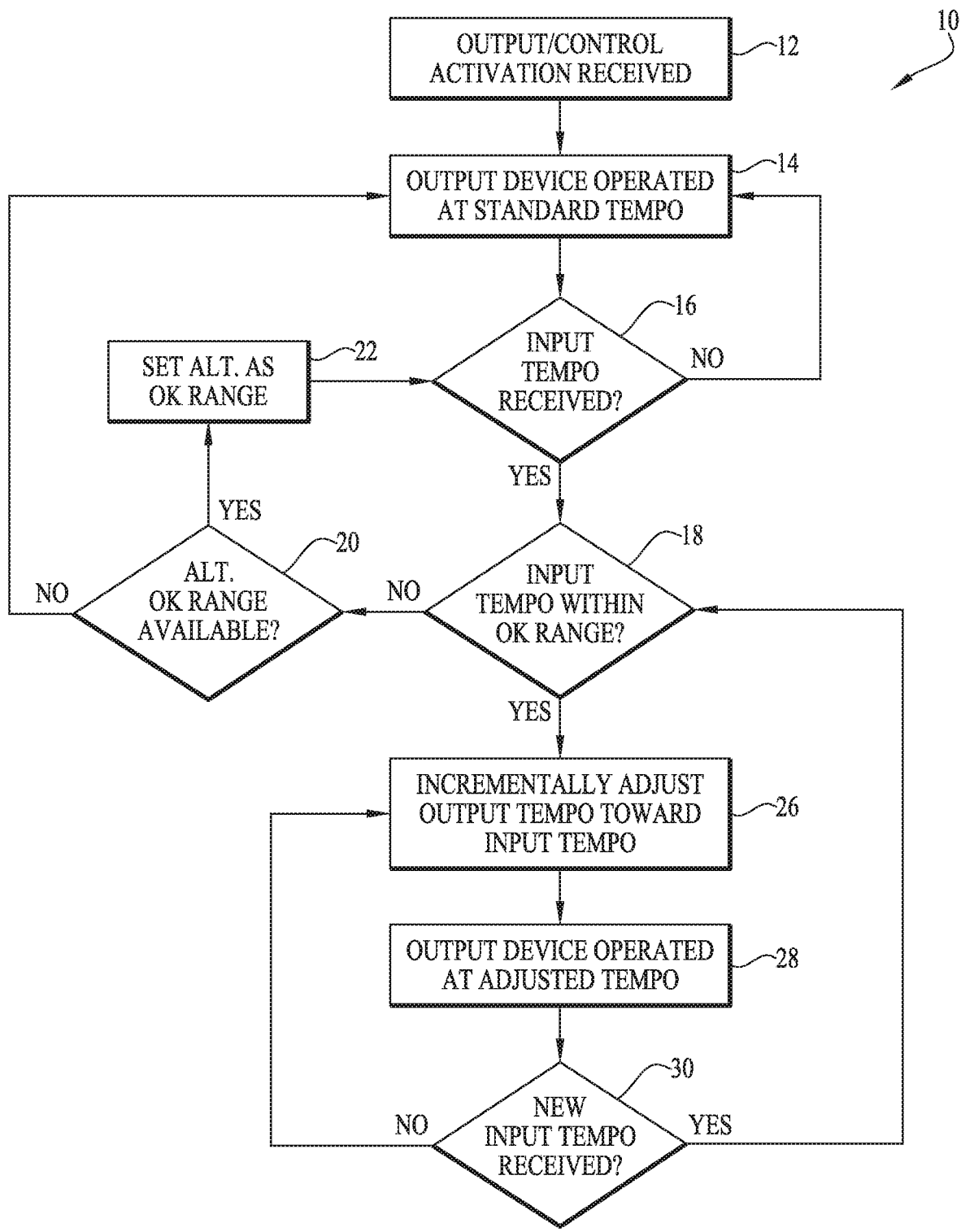
FIG. 1 is a flow diagram showing a method of adapting sensory outputs for synchronization to input tempos for providing soothing and/or other effects according to an example embodiment.

With reference now to the drawing figures, wherein like reference numbers represent corresponding parts throughout the several views, FIG. 1 shows a method 10 of adapting sensory outputs for synchronization to input tempos for providing soothing and/or other effects according to an example embodiment of the present disclosure. The method 10 can be implemented by computer-based devices and systems for example as described herein.

The adaptive sensory output method 10 includes at 12 receiving an activation signal for example a selection of an output mode and/or a selection of a particular output. Some embodiments include multiple output modes, such as music content, video content, haptic pulses, oscillating motions, other motions, and/or light shows. Some embodiments include multiple outputs within one or more output modes, such as a menu of songs and/or multiple motion speed settings (e.g., slow, medium, and fast). For an embodiment including only one output mode and only one particular output, the activation signal can be a "power on" signal.

At 14 an output device is operated to output the particular output selection at its standard (normal) tempo. The particular output selections each have a respective standard (normal) tempo. As used herein, the term "tempo" refers generally to rhythms, cadences, pulses, beats, rates, paces, patterns, oscillations, cycles, and other repeating (e.g., sinusoidal) waveforms producing sound, touch, motion, or light. As such, the adaptive sensory output method 10 can be implemented to produce many (if not all) sensory experiences that involve the sensing of sounds, touches, motions, and/or sights that have a tempo.

If an input tempo is not received at 16, then the output device continues to operate by outputting the output selection at its standard tempo. As used herein, the term "input" refers generally to biorhythms that have a variable tempo, for example heartrates (e.g., pulses or beats per minute), respiratory rates (e.g., breaths per minute), gaits (e.g., steps per minute), and so forth. Also, the term "input" can refer generally to other measurable inputs that have variable tempos, for example haptic pulses and oscillatory motions.

If an input tempo is received at 16, then at 18 it is compared to a permissible (i.e., acceptable or "OK") tempo range for the output selection. The particular output selections each have a respective OK tempo range, with the respective standard tempo being within that range and typically at its midpoint or centerline. Within the OK tempo range, the output tempo is perceived as being close-enough to the standard tempo that the difference is not readily noticeable to average persons.

If the input tempo is not within the OK tempo range at 18, then at 20 a look-up is made for an alternative output selection with an OK tempo range bracketing the input tempo. As noted above, some embodiments include multiple output selections, such as multiple songs and/or multiple motion-speed settings.

If an alternative output selection with an OK tempo range is not available at 20, then the output device continues to operate by outputting the output selection at its standard tempo. But if one is available, then that is set as the updated OK tempo range at 22, and at 16 the loop continues until an input tempo is identified that is within the OK tempo range at 18.

Having identified an in-range, the process 10 moves on to 26. There, the output tempo is incrementally adjusted (faster or slower, as appropriate) toward the input tempo. If the difference in the output and input tempos is very small, for example not readily perceivable by average persons, then effectively the output tempo can be adjusted to the input tempo in one step. But typically the difference is large enough that such a one-step adjustment would be readily noticeable by average persons. So typically the output tempo is adjusted (adapted) toward the input tempo by an incremental amount that is small enough that the change is not readily noticeable by average persons.

At 28, the output device continues to operate but now by outputting the output selection at the adjusted tempo. So the output selection, for example a song or soothing rhythmic sound (e.g., ocean waves), now has a tempo that is closer to the input tempo, for example a heartbeat or other biorhythm of a parent, to provide an even more soothing experience to a child hearing the parent-heartbeat-synched rhythmic sounds.

If an updated input tempo is not received at 30, then the process 10 returns to 26 to continue refinements by making further incremental adjustments to get the output tempo closer to the previously received input tempo. This way, the output does not have to either stop or "jump" back to its standard tempo, either of which would typically not provide a positive user experience. And if an updated input tempo is received, then the process returns to 18 to continue refinements by making incremental adjustments to get the output tempo closer to the newly received input tempo. As the input tempo typically changes continuously over time, whether due to a decreasing heartrate during calming conditions or variations or drift in mechanical systems, the process 10 can continue with the output tempo tracking toward but never matching/equaling the input tempo.

The process 10 thus functions to operate the output device at an adapting tempo that trends toward an input tempo, when available, and when not, that outputs using a standard tempo. The process 10 concludes upon the output selection coming to completion, after a predetermined time period, upon a powering off, etc.

In the depicted embodiment, the adapting output tempo tracks toward the input tempo with the goal of matching the output tempo to the input tempo for synchronization. In other embodiments, the adapting output tempo tracks toward a harmonic of the input tempo, so the tempos are not intended to match but are still synchronized. For example, a song can be played at a tempo that is a ratio (e.g., half) the elevated heartrate of an exercising parent to provide for parent-child engagement and connection without the child becoming stressed from the fast tempo. As another example, the adapting output tempo can be phase shifted relative to the input tempo.

Figure 2:
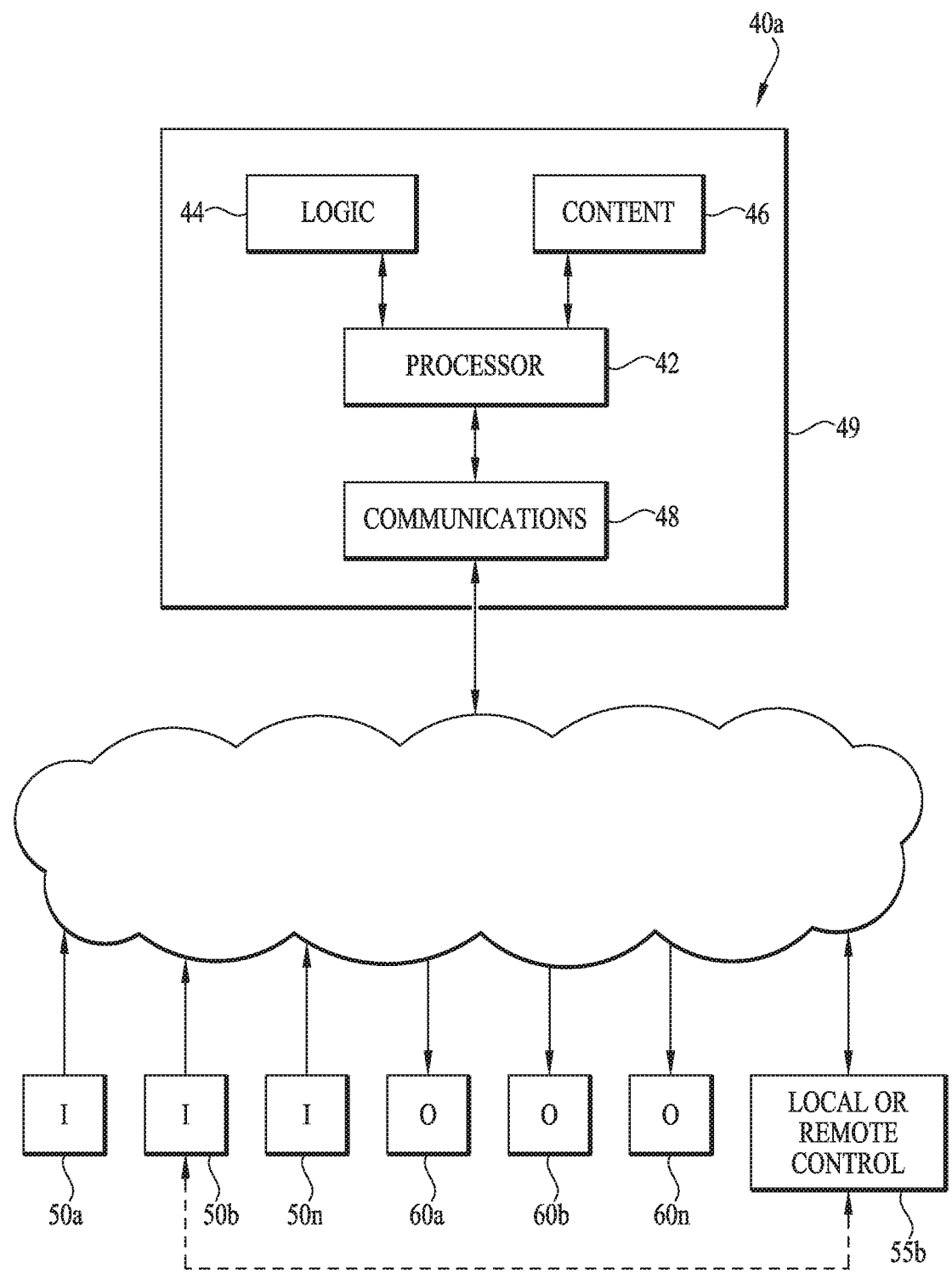
FIG. 2 is a block diagram of a system for implementing the adaptive sensory output method of FIG. 1 according to an example embodiment.
Figure 3:
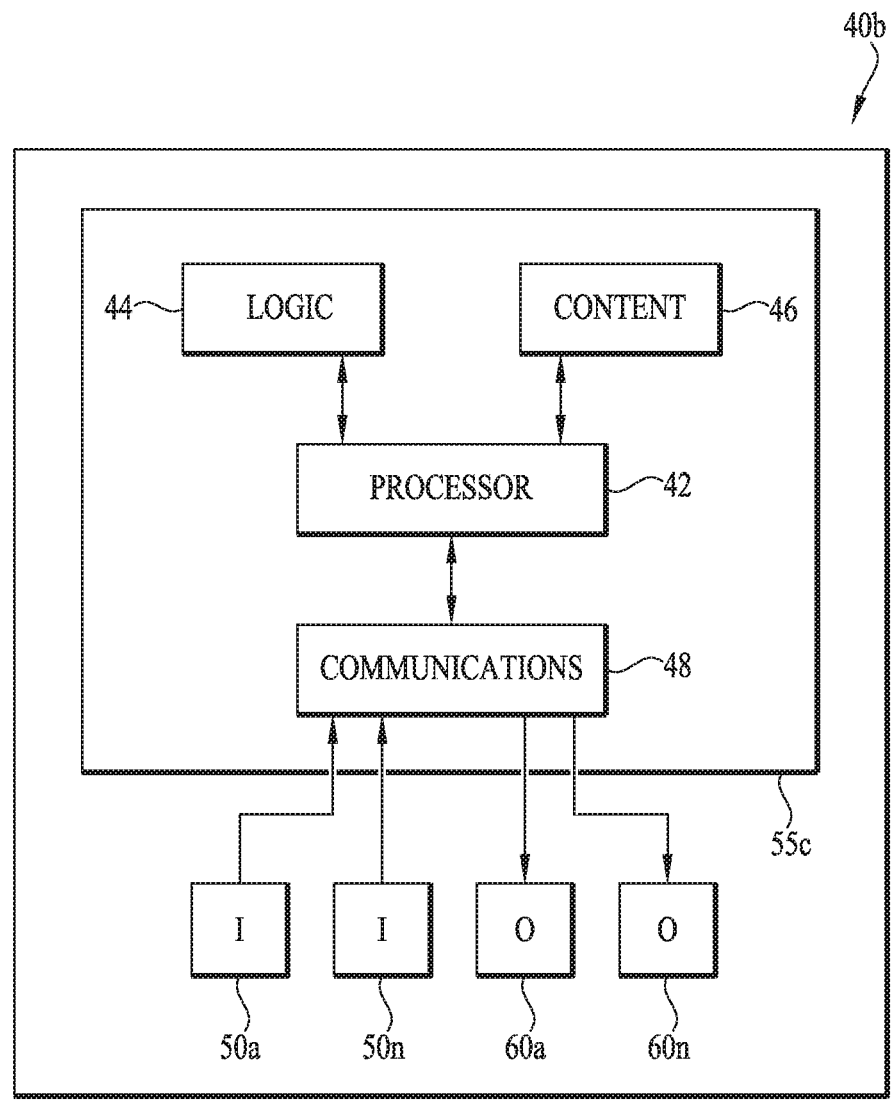
FIG. 3 is a block diagram of a device for implementing the adaptive sensory output method of FIG. 1 according to an example embodiment.
Figure 4:
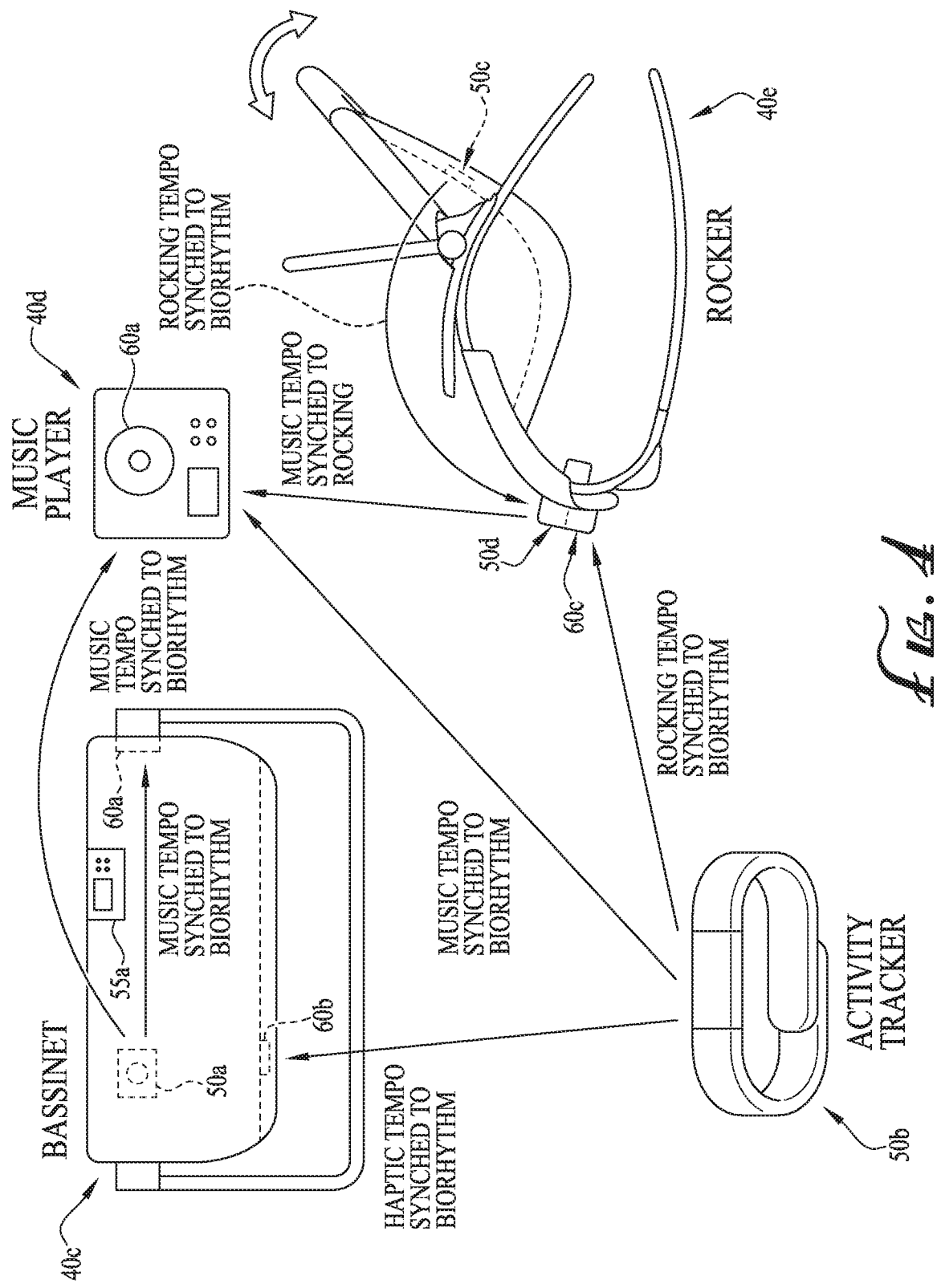
FIG. 4 is a schematic diagram of example embodiment systems and devices of FIGS. 2 and 3 for implementing the adaptive sensory output method of Figure

FIGS. 2-4 show various example systems and devices 40a-n (collectively the "systems 40" and/or the "devices 40") for implementing the adaptive sensory output method 10 of FIG. 1. In particular, FIGS. 2 and 3 show an example system 40a and an example device 40b in schematic form, and FIG. 4 shows a network of such example systems and devices 40 in the infant-care market.

Referring particularly to FIG. 2, the adaptive sensory output system 40a includes a processor 42, stored logic 44, stored content 46, and communications components 48. The processor 42 can be for example a conventional general-purpose computer processor. The logic 44 and the content 46 can be stored on a computer-readable memory device (e.g., non-transitory) for example a conventional optical or magnetic hard drive. The logic 44 includes instruction sets that are read and interpreted by the processor 42 to implement the adaptive sensory output method 10. The content 46 can include music/songs, other rhythmic sounds (e.g., ocean waves, birds chirping, wind blowing, frogs croaking, rain falling, and/or crickets chirping), videos, and other pre-loaded content that can be output by the output devices (described below) to produce outputs that are sensible by sight, sound, or touch by humans and other animals. And the communications components 48 can be of a conventional type, for example a wireless connection (e.g., a transceiver and antenna) or a wired connection, for communicating with input and output devices (described below) to implement the adaptive sensory output method 10.

The input devices 50*a-n* (collectively the "input devices 50") and the output devices 60*a-n* (collectively the "output devices 60") communicate via the communications components 48 to implement the adaptive sensory output method 10. The input devices 50 can be conventional devices that include a sensor that senses a tempo (e.g., relatively slowly changing but meaningful) and communications components that send a signal representing the tempo to the processor 42 for processing using the logic 44.

Some example input devices 50 will now be described with reference to FIG. 4. One example input device is a conventional biorhythmic sensing device 50*a* that includes a camera or radar that images a child, software that uses algorithms to determine the respiratory rate of the child from the image stream, and communications components that transmit the respiratory rate data. Other example input devices include activity trackers (e.g., FITBIT and GARMIN trackers) 50*b* that include sensors (e.g., accelerometer and galvanic skin response) to measure the wearer's heartrate, respiratory rate, and/or steps/gait. Yet another example input device is a conventional biorhythmic sensing device 50*c* that includes an infrared reflection sensor that senses a pulsing amplitude to identify the heartrate of a person in contact with it. And still other example input devices include an accelerometer 50*d* with programming for identifying an oscillating motion tempo (like in an activity tracker, but for a mechanical rocker, swing, etc.). It will be understood that these are examples only and not an exhaustive listing of possible input devices, as broadly defined above.

The output devices 60 can be conventional devices that include communications components that receive a signal including the standard or adjusted tempo as determined using the logic 44 and that function to produce a rhythmic output at the received tempo. Some example output devices 60 will now be described with reference to FIG. 4. One example output device is a conventional audio speaker 60*a* that plays songs and other sounds based on a received audio signal (an amplifier can be integrated into the speaker housing or provided separately for example in a control unit 55*a*). Another example input device is a conventional haptic pulsing device 60*b* that includes a vibrator or other mechanical drive that produces a pulsing haptic tempo to simulate a heartbeat based on a received tempo signal. And still other example output devices include a motor (or other motion-imparting mechanism) 60*c* that is driven to produce an oscillatory (e.g., rocking or swinging) motion in a mechanical device (e.g., a rocker or swing) that it mounts to or engages based on a received tempo signal. For output devices that play sounds, the output signal includes the content (e.g., music) at the tempo it is to be played at (or only tempo data if the content is stored locally), and for haptic or motion output devices, the output signal includes the tempo that the output device is to be driven at to produce the haptic pulses or oscillating motion. Other output devices can be provided that include lamps that emit light patterns with a tempo. It will be understood that these are examples only and not an exhaustive listing of possible output devices, as broadly defined above.

Continuing with reference to FIG. 2, the adaptive sensory output system 40*a* is configured with the processor 42, logic 44, content 46, and communications 48 remotely located on one or more computer servers 49, for example in the "cloud" or another distributed computer network arrangement. The input devices 50 and the output devices 60 can be located at the user's home, at various locations (e.g., grandparent's home and vacation home), and/or they can be portable for relocating as desired. And the server(s) 49 and the input and output devices 50 and 60 communicate via a communications network such as the internet, a cellular network, or a wireless (WiFi) hotspot.

In addition, a local control unit 55*a* or 55*b* can be included for providing the basic operational controls (e.g., power on/of, volume, speed settings, output mode/device), output selections (which particular in-range song, etc.), and/or input selections (which particular type of biorhythm, etc.) for the output devices 60. For example, a local control unit 55*a* can be included in a juvenile product for this purpose and also for housing wireless communications components (with wiring to the output devices 60). As another example, a local control unit 55*b* can be in the form of an "app" that can be downloaded onto a parent's smartphone and used for this purpose. For app-type control units 55*b*, the communication components of the smartphone can be used to communicate with the input devices for example using BLUETOOTH technology (as indicated by the dashed line connecting 50*b* and 55*b* in FIG. 2). Also, for use with third-party input devices such as activity trackers 50*b*, the app can include a feature for "pairing" with the tracker to enable the transmission of biorhythmic tempo input data.

As just described, the adaptive sensory output system 40*a* of FIG. 2 is a networked arrangement that can be implemented for example using an Internet-of-Things (IoT) approach. FIG. 3 shows a related adaptive sensory output device 40*b* that is similar but implemented in a single product. Thus, the device 40*b* includes the processor 42, logic 44, content 46, and communications 48 locally located, for example in a local control unit 55*c* that is integral to the device 40*b*. And the device 40*b* includes local (e.g., integral or attachable) input devices 50 and local output devices 60 (e.g., integral or attachable), which can communicate with the control unit 55*c* by wired connections.

As noted above, a primary application of the adaptive sensory output method 10 and systems/devices 40 is infant-care products. As also noted above, however, the adaptive sensory output method 10 and systems/devices 40 can be readily adapted for use in other applications such as elderly care products (e.g., rocking chairs), pet-care products, and general entertainment and relaxation products (e.g., relaxation chairs that provide massages and play music).

In addition, some embodiments in the infant-care and other product applications are configured to produce water-marking/inaudible sounds to make the output device light up or vibrate/move according to the particular output selection (e.g., song) that is being played. Also, in some embodiments the output devices can additionally be used as a nightlight.

FIG. 4 shows an array of representative embodiments to further illustrate some of the many infant-care applications of the adaptive sensory output method 10 and systems/devices 40. These include a bassinet 40*c* that includes features of the system 40*a* and the device 40*b*. The bassinet 40*c* includes an integral biorhythmic input device 50*a* that detects the respiratory rate of a child in the bassinet and an integral audio speaker output device 60*a* that plays sounds synched to the child's respiratory rate to provide a soothing effect to the child (in accordance with device 40*b*). The biorhythmic input device 50*a* of the bassinet 40*c* can alternatively or additionally transmit the child's respiratory rate data to a non-integral/separate (e.g., in the same home, in the same or a different room) audio speaker output device 60*a* of a music player 40*d* that plays sounds synched to the child's respiratory rate to provide a soothing effect to the child (in accordance with system 40*a*). In addition, the bassinet 40*c* includes an integral biorhythmic output device 60*b* that produces haptic pulses in the padding/matt on which the child rests to simulate for example a parent's heartbeat based on the input tempo from the heartrate data received from a non-integral/separate activity tracker input device 50*b* worn for example by the parent. The bassinet 40*c* can also include a control unit 55*a* for operational control of these input and output devices 50*a*, 60*a*, and 60*b*.

Another representative example depicted in FIG. 4 is the music player 40*d* that can receive biorhythmic data from the activity tracker input device 50*b* and play for the child a song with a tempo synched to the parent's heartrate to provide a soothing effect to the child. Similarly, the music player 40*d* can receive rhythmic tempo data from an oscillatory-motion-sensing input device 50*d* integral to a children's rocker 40*e* and adapted to determine the oscillatory tempo of the rocker 40*e*, and the music player 40*d* can play for the child a song with a tempo synched to the rocking tempo of the rocker to provide a soothing effect to the child. The music player 40*d* can also include a control unit for operational control of the output device 60*a*.

Yet another representative example depicted in FIG. 4 is the children's rocker 40*e* that includes an integral motion-imparting output device 60*c* that can operate to produce or drive a rocking motion of the rocker 40*e* at a tempo synched to the parent's heartrate based on the biorhythmic data received from the activity tracker input device 50*b* to provide a soothing effect to the child. Similarly, the rocker 40*e* can include an integral haptic-sensing input device 50*c* that is located in the matt or bedding that the child rests upon, that detects the heartrate of a child resting in the rocker, and that transmits the heartrate data to the integral motion-imparting output device 60*c*, which in turn operates to rock the rocker 40*e* at a tempo synched to the child's heartrate to provide a soothing effect to the child. The rocker 40*e* can also include a control unit for operational control of these input and output devices 50*c*, 50*d*, and 60*c*.

To assist in a fuller understanding of the disclosure, an example use including a music wind-down use and a subsequent haptic heartbeat use will be described. For the music wind-down use, consider the situation where mom's daily workout is interrupted by a monitor indicating that her infant child is awake. Mom picks up her daughter wrapped in a blanket and lays her daughter on her chest. She taps the music player 40*d* on the nearby table. The music player 40*d* receives respiration rate data from mom's fitness tracker 50*b* and auto-selects an up-tempo song from the built-in content library that best matches her current respiration rate. The music tempo then synchronizes to the up and down motion of mom's chest, thereby comforting both mom and daughter. As mom's respiration rate gradually slows/calms down, the musical melody tracks with the slowing rate inducing a calming effect on both mom and daughter until the latter becomes very sleepy.

For the subsequent haptic heartbeat use, mom then lays her daughter down in the nearby bassinet 40*c*. She sits in a chair watching her daughter continue to drift back towards sleep. Mom reaches over and taps on the UI/UX control panel 55*a* to turn on the haptic pulse output device 60*b* to produce a slow pulsing vibration starting at 1 pulse per second (60 BPM). When mom's fitness tracker 50*b* provides updated data on her heartrate, the haptic pulsing output is then slewed from 60 BPM towards the updated heartrate. The child can still feel the slow pulse of mom's heart even after she's left mom's chest for a soothing sensory experience.

These example embodiments are representative of the many infant-care applications of the adaptive sensory output method 10 and systems/devices 40. Additional example embodiments include bouncers, swings, play yards, strollers, children's car seats, educational toys, and other juvenile products.

The described and additional example embodiments, and their design and benefits, may be better understood in light of the following details relating to the tempo inputs and adapted tempo outputs. With respect to the acquisition of biorhythm data, before the sensory experience can be dynamically adapted, an input reference source of slowly changing but meaningful tempo data must first be acquired from an input device 50. With respect to respiratory rates, synchronizing a soothing experience to the respiratory rate of the child (e.g., occupant) provides a constructive enhancement of any movement experience in the juvenile product by stimulating two or more senses or two instances of the same sense (e.g. touch) in concert. As an infant breathes in and out, the peak amplitudes of a rocking or swinging motion can be adjusted to match, creating both a physical and mental complement to natural breathing. Persons often naturally and instinctively match breathing during exercise to the movements of the activity.

Capturing the respiratory rate can be performed through a variety of means. One example is the auto-correlation of micro-movements in sensor inputs. For example, sensitive motion accelerometers register Newtonian opposite forces captured in mechanical supports as the center of mass of an infant changes due to diaphragm movement. These signals are minimal and barely register above ambient noise captured by the sensors. However, because the respiratory rate is periodic, an auto-correlation of the signal causes the movement to multiply with itself over time and a signal spike to rise above the noise. The ambient or common noise is Gaussian and self-cancels. This sort of auto-correlation is common in activity (fitness) trackers to acquire respiratory and heart rates from both motion and infrared light sensors. Respiratory rate information can come from a local sensor suite (e.g., input devices 50*a* and 50*c*) or be provided by third-party devices such as fitness trackers (e.g., input device 50*b*) through a connected information portal.

With respect to heartrate, a baby spends nine months in mom's womb. For most of that time, the only consistent experience is the steady metronome of mom's heartbeat. After birth, an infant spends significant time on mom's chest and in her arms where the cadence of mom's heart beating may provide a familiar calming rhythm. In the soothing experience, the tempo of rhythmic outputs, such as music or an oscillating movement of mechanical elements, is adjusted to the real-time capture of mom's heart rate. Most fitness trackers provide heartrate capture through auto-correlation of infrared receivers or skin contact galvanic sensors.

With respect to oscillatory movement, some rockers and other motional devices include a self-propelled mechanism that produces a closed periodic pattern of oscillating movement, and they can be adapted to sense/detect the tempo of oscillation of the motional device. Additionally, for impromptu movements, a rocking chair can be adapted to play music at an adjusted tempo based on the rocking tempo of the chair (non-self-propelled) caused by a senior is tapping their foot to slowly move the chair back and forth rhythmically.

With respect to audio outputs, some embodiments include additional processing for providing the soothing functionality described herein. Musical compositions are paced at an often static but sometimes dynamic tempo, usually expressed in beats per minute (BPM). Typically, performances of the musical composition are paced at the standard/intended BPM as authored to establish a pattern of familiarity and correctness to the listener. However, if a musical composition is played "fast" (at a higher BPM) or "slow" (at a lower BPM), a listener typically still recognizes the composition based on the clear progression of notes. If the speed difference is small enough, many listeners may not even notice the tempo/speed change unless they are very familiar with the composition from prior performances of it, or have a very acute sense of musical timing. If the tempo/speed difference starts at zero (matching the standard tempo) and varies at a slow enough rate of change, even a listener with a trained sense of timing and high familiarity with the composition and past performances of it may not even notice the minor difference in tempo.

Based on this, some embodiments of the disclosure function to limit the incremental tempo adjustment of a musical composition to a small tempo delta (e.g., at step 26 in method 10) and include a library/collection of related musical compositions (e.g., stored in content 46) with standard tempos spaced within the same tempo delta of each other. This enables matching any given input (biorhythmic) tempo with a larger field of musical output options.

Figure 5:
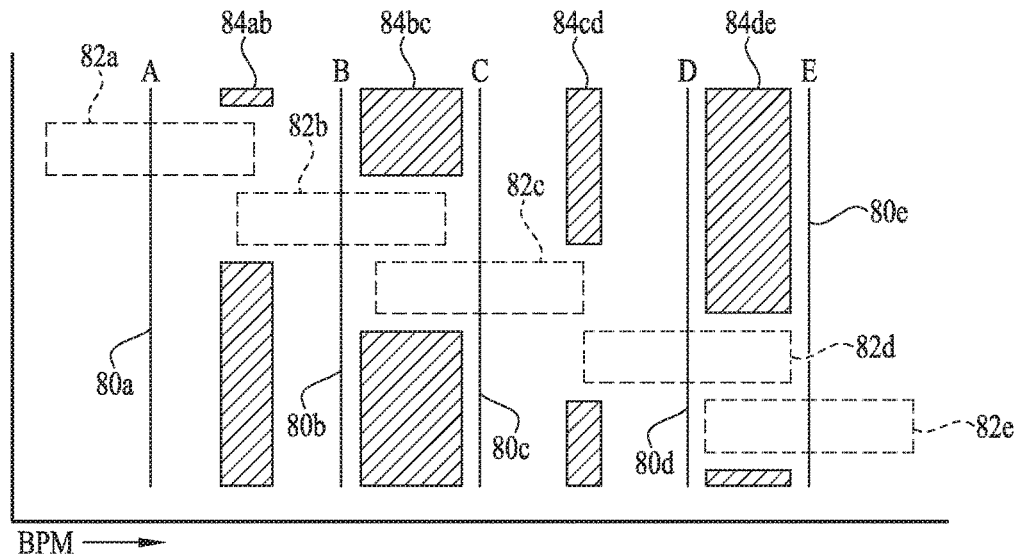
FIG. 5 is a graph showing example acceptable tempo ranges for different songs for use in the method of FIG. 1.

As shown in FIG. 5, each musical composition A-E has a standard playback tempo 80*a-e* on the horizontal tempo scale. The musical compositions A-E are selected to have standard tempos 80*a-e* that are close enough to each other, and permissible/OK tempo ranges 82*a-e* that include overlapping regions 84*ab-de* between adjacent permissible/OK tempo ranges on the slow and fast sides on the horizontal tempo scale. In this way, any input tempo can be matched to at least one musical composition with an OK tempo range (e.g., 82*c*) spanning the input tempo. And as the input tempo changes beyond the OK tempo range 82*c*, the output musical tempo can be sped up or slowed down to fall within an adjacent and overlapping OK tempo range 82 *b* or 82*d* of at least one other musical composition that is available for playback (see step 20 of method 10).

Both upon the initial acquisition of the biorhythm input tempo reference and during musical playback, the tempo of the soothing audio playback signal is typically never hard-synchronized to the input biorhythm tempo reference. That is, it is rarely if ever set equal to the biorhythm input tempo in one update cycle, as noted above. Instead, the biorhythm input tempo is used as a desired ideal or target for a gradual slew of the current playback output tempo. This can involve two parameters that can be included in the method 10 described above. First is including a maximum amount of tempo change per unit time, which limits gross changes in discrete updates to the playback rate (i.e., the "tempo delta" discussed above and also with reference to step 26 of method 10). And second is including a differential tempo update rate per unit time as a percentage of the difference of the current playback rate and the input biorhythm tempo reference, which ensures the actual playback rate tracks and slews gradually and asymptotically towards the input biorhythm tempo reference over time, even if the input biorhythm tempo reference is continuously changing. That is, the tempo update interval (see FIG. 6) can be decreased (to increase the update frequency/rate) to provide more frequent and thus more-precise output tempo adjustments, or it can be increased (to decrease the update frequency/rate) if less frequent and thus less-precise output tempo adjustments are acceptable or preferred in a given application. In some embodiments, tempo update interval is monotonic, with only the delta update changing at each update period.

Figure 6:
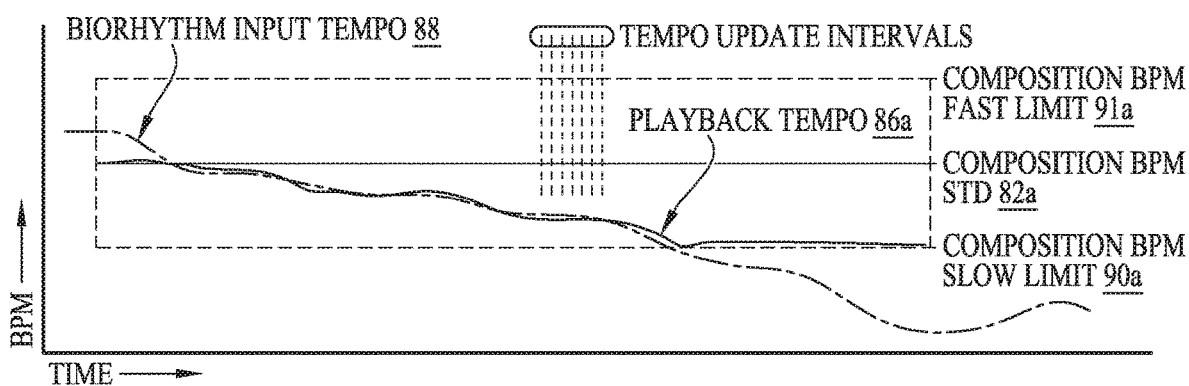
FIG. 6 is a plot of tempo versus time showing changing tempo inputs and an acceptable tempo range of a playing song for use in the method of FIG. 1.

As shown in FIG. 6, when the musical composition starts, its playback/output tempo 86*a* is at the standard (original/intended) playback rate 82*a* (step 14 of method 10). In this example, at time zero the input biorhythm tempo reference 88 is about 40% faster than the standard playback rate 82*a* relative to the maximum slewable speed of the musical composition. As time progresses, the actual playback tempo 86*a* chases the constantly changing target input tempo reference 88, often crossing the target line but typically never perfectly in-sync with it. This tracking continues until the target input tempo reference 88 exceeds the lower playback tempo rate 90*a* defined by a meta-attribute of the stored composition (i.e., the slow limit of the OK tempo range 82*a*), or alternatively until it exceeds the fast limit 91*a*. If the playback output tempo 86*a* were to exceed the lower rate limit 90*a*, the likelihood of a listener interpreting the playback as distorted increases. So if only composition A exists in the content library 46, the playback rate 86*a* continues at the lower limit 90*a* for composition A while the target tempo reference 88 continues below it. This feature helps ensure the quality of the soothing experience.

Figure 7:
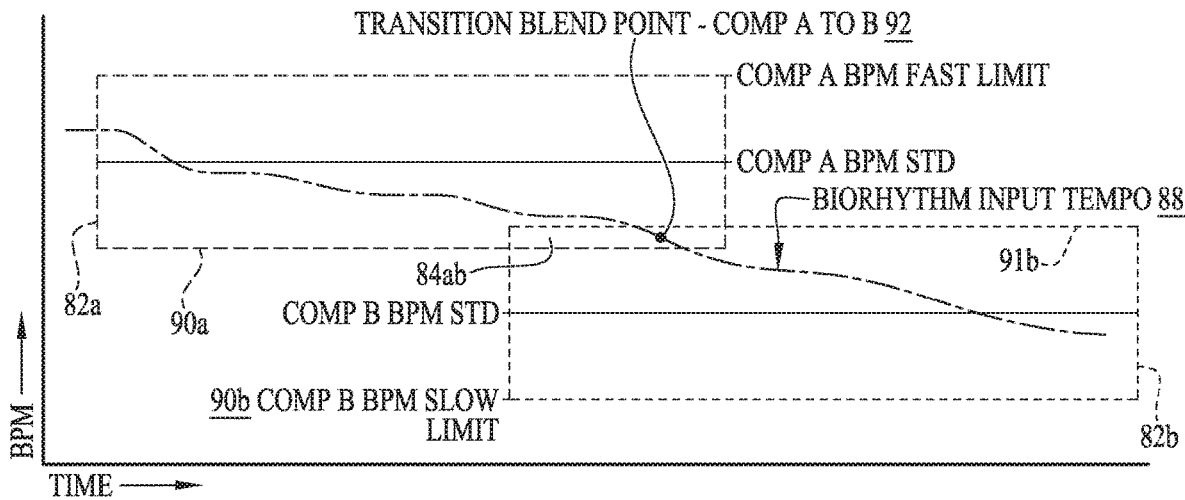
FIG. 7 is a plot of tempo versus time showing two overlapping acceptable tempo ranges for two songs for use in the method of FIG. 1.

FIG. 7 shows two musical compositions A-B stored in the content library 46 and selected with OK tempo ranges 82*a-b* having an overlapping tempo region 84*ab*. In this example, the additional of composition B enables a switching between songs. So instead of the playback rate 86*a* continuing at the lower limit 90*a* for composition A while the target tempo reference 88 continues below it, as in FIG. 6, in this example, the payback switches to composition B and the audio playback tempo (not shown) continues tracking towards the falling target tempo reference 88. As the target tempo reference 88 nears the lower limit 90*a* for composition A, composition B can be started in parallel at zero volume and at the same output BPM (not shown) as composition A. If the target tempo reference 88 then drifts back up, or if it is determined based on historical rate information that it is likely to (using algorithms, AI, etc. of a convention type), the composition A can continue to be played. This determination can be made dynamically and repeatedly as the difference between the current limited playback rate 86*a* and tempo reference 88 continues to change.

But if the target tempo reference 88 continues to drift downward, then while in the overlapping tempo region 84*ab* (still above the slow limit 90*a* of composition A, but now below the fast limit 91*b* of composition B), there is a transition point 92 at which the playback output is switched from composition A to composition B. At the transition point 92, the playback volume of composition B can be slowly raised while that of composition A can be slowly lowered (e.g., in a cross-fade technique providing a smooth transition) to make composition B the updated/current playback content (see step 22 in method 10). This cross-fade allows further room to continue to slew the playback tempo of composition B down towards the target tempo reference 88 until it hits composition B's lower limit 90*b*. This progression can continue down and up to limits established by the slowest and highest tempo compositions in the content library 46.

The same methodology can be applied when the output is mechanical movement, be it a haptic pulse in the padding of a child-supporting device, an oscillatory motion of a child-supporting device, or another conventional mechanical system. That is, the speed/tempo of mechanical actuation (e.g., of a vibrator for haptic pulses or a motor for a rocking or swinging motion) can be adapted to track a target tempo reference of any of the types described herein. In this way, any movement of the child-supporting device or other product, such as rocking motion, rotation of accessories or secondary movements, and haptic motors and vibration functions, can be adjusted in the same fashion as the audio tempo in BPM.

Figure 8:
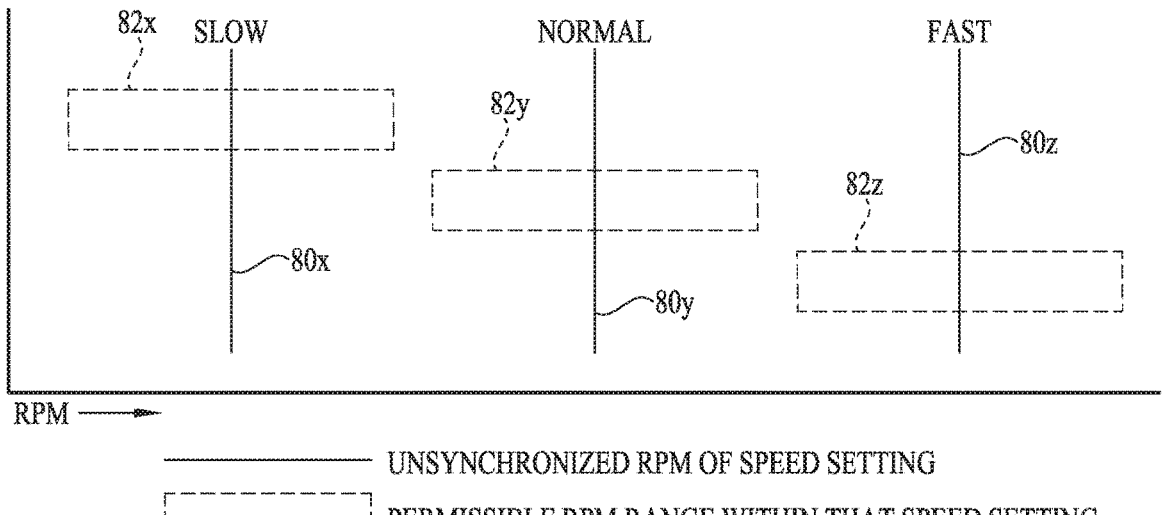
FIG. 8 is a graph showing example acceptable tempo ranges for different motion speed settings for use in the method of FIG. 1.

Referring to FIG. 8, mechanical motion is generally expressed in cycles per unit time, for example, revolutions per minute (RPM). Typically, products with speed controls have speed settings that are not based on the actual RPM/speed settings, but instead that are provided as discrete general settings such as "Slow," "Normal," and "Fast." Each of these speed settings has a permissible/OK tempo range $82x$-$y$ bounded by respective lower limits $90x$-$z$ and respective upper limits $91$ $x$-$z$. Typically, the OK speed ranges $82x$-$z$ do not overlap, because typically the running output speed is not automatically adjusted between speed settings to provide for user control (e.g., a user may not want a rocker to swing fast when originally set to slow). That is, for mechanical motion applications, the methodology of FIG. 6 is typically used, not that of FIG. 7.

When the user activates a mechanical product (such as a rocker or other child-supporting device) to produce an oscillating motion at a user-selected slow speed setting, the motion is typically started at the standard tempo $80x$ (typically the center line of the OK range $82x$). A target input tempo reference (e.g., a biorhythmic input tempo) is acquired and compared against the selected OK speed range $82x$. If it consistently (over a predefined time period) lies outside of the OK speed range $82x$, the motion tempo is not adjusted, and a "no motion tracking" or similar indicator can be activated to notify the user of the out-of-range condition so the user can consider selecting another input tempo/device or output device. If the target input tempo consistently lies within the OK speed range $82x$, the current output rate of oscillatory motion is gradually slewed towards the target input tempo reference (e.g., in the same manner as for audio BPM as described above). If the target input tempo reference drifts outside of the OK speed range $82x$, pulling the motion frequency to the limits $82x$ of the speed settings, then the output speed can be gradually returned to the standard frequency until another in-range target input tempo is acquired.

Furthermore, the systems/devices 40 and methods 10 for adaptive sensory outputs are not restricted to tracking/synchronizing to a single input tempo 88 at a time. Instead, multiple input tempo signals 88 can be tracked simultaneously, such as mom's heartrate as sensed by an activity tracker 50*b*, daughter's heart and respiration rates tracked by sensors 50*a* on a bassinet 40*c*, a manually initiated rocking motion (e.g., with a foot or hand) of a rocker 40*e* identified by an onboard sensor 50*d*, and/or other rhythmic inputs whether existing or not. With multiple target tempo reference signals 88 received, each may be compared to the audio content library 46, optional speed settings, etc. for an in-range determination. The target tempo references 88 may be selected automatically by the product, restricted based on user-specified lock-outs, or selected with affinity considerations as defined by the operator.

While the disclosure includes a number of example embodiments, it will be understood by those skilled in the art that a variety of modifications, additions and deletions are within the scope of the invention, as defined by the following claims.

What is claimed is:

1. A computer-implemented adaptive sensory output method, comprising:
   receiving an input tempo from an input device;
   determining if the input tempo is within a permissible tempo range for a sensory output selection;
   if not in-range, operating an output device to output the sensory output selection at a standard tempo for the sensory output selection; and
   if in-range, operating the output device to output the sensory output selection at an adjusted tempo that is synchronized to the input tempo,
   wherein the synchronization of the adjusted tempo of the sensory output selection to the input tempo provides a soothing experience,
   wherein the in-range step comprises first operating the output device to output the sensory output selection at the standard tempo and then incrementally slewing the adjusted tempo toward synchronization to the input tempo.

2. The method of claim 1, further including the step of identifying if an input tempo has been received, if received then proceeding with the method, and if not received then operating the output device to output the sensory output selection at the standard tempo.

3. The method of claim 1, further including repeating the steps over time in regular intervals so that as the input tempo changes over time the adjusted tempo changes over time to track it.

4. A computer-implemented adaptive sensory output method, comprising:
   receiving an input tempo from an input device;
   determining if the input tempo is within a permissible tempo range for a sensory output selection;
   if not in-range, operating an output device to output the sensory output selection at a standard tempo for the sensory output selection;
   if in-range, operating the output device to output the sensory output selection at an adjusted tempo that is synchronized to the input tempo, and
   repeating the steps over time in regular intervals so that as the input tempo changes over time the adjusted tempo changes over time to track it;
   wherein the synchronization of the adjusted tempo of the sensory output selection to the input tempo provides a soothing experience, and
   wherein, if the input tempo is no longer received, incrementally slewing the sensory output selection to the standard tempo.

5. The method of claim 1, wherein, in the in-range step, if the adjusted tempo is adjusted to a tempo limit of the permissible tempo range for the sensory output selection, and if the input tempo changes past the tempo limit to outside of the permissible tempo range, then operating the output device to output the sensory output selection at the tempo limit.

6. The method of claim 1, wherein, in the in-range step, if the adjusted tempo is adjusted to a tempo limit of the permissible tempo range for the sensory output selection, and if the input tempo changes past the tempo limit to outside of the permissible tempo range, then transitioning to output a next sensory output selection having a respective next permissible tempo range spanning the changed input tempo.

7. The method of claim 1, further including receiving a user selection of the input tempo to receive, the input device to receive the input tempo from, the sensory output selection to output, the output device to operate, or a combination thereof.

8. The method of claim 1, wherein the input tempo is a biorhythmic tempo and the input device is an activity tracker or a haptic pulse sensor.

9. The method of claim 1, wherein the input tempo is a rhythmic tempo of an oscillating motion or a haptic pulse.

10. The method of claim 1, wherein the sensory output selection includes audible sounds and the output device includes an audio speaker.

11. The method of claim 1, wherein the sensory output selection is haptic pulses or an oscillating motion and the output device includes a haptic pulsing vibrator or a drive device for imparting oscillating motion.

12. A non-transitory computer-readable storage device storing instructions for performing the method of claim 1.

13. A computer-implemented adaptive sensory output method, comprising:
  receiving an input tempo from an input device;
  determining if the input tempo is within a permissible tempo range for a sensory output selection;
  if not in-range, operating an output device to output the sensory output selection at a standard tempo for the sensory output selection; and
  if in-range, operating the output device to output the sensory output selection at an adjusted tempo that is synchronized to the input tempo,
wherein the synchronization of the adjusted tempo of the sensory output selection to the input tempo provides a soothing experience,
wherein, in the in-range step, if the adjusted tempo is adjusted to a tempo limit of the permissible tempo range for the sensory output selection, and if the input tempo changes past the tempo limit to outside of the permissible tempo range, then transitioning to output a next sensory output selection having a respective next permissible tempo range spanning the changed input tempo,
wherein the permissible tempo range for the sensory output selection and the next permissible tempo range for the next sensory output selection have an overlapping tempo region, and wherein the step of transitioning to the next sensory output selection is done when the input tempo is within the overlapping tempo region.

14. An adaptive sensory output arrangement, comprising:
  at least one memory device operable to store computer-executable instructions; and
  at least one processor configured to execute the instructions to:
    receive a heartrate input tempo from an input device associated with a caretaker;
    determine if the heartrate input tempo is within a permissible tempo range for a sensory music output selection;
    if not in-range, operate an output device to output the sensory music output selection at a standard tempo for the sensory music output selection;
    if in-range, operate the output device to output the sensory music output selection at an adjusted tempo that is synchronized to the heartrate input tempo; and
    repeat the steps over time in regular intervals so that as the heartrate input tempo changes over time the adjusted tempo changes over time to track it;
  wherein the synchronization of the adjusted tempo of the sensory music output selection to the heartrate input tempo provides a soothing experience directed to a juvenile.

15. The arrangement of claim 14, wherein the memory device further stores a library of audio content from which is selected the sensory music output selection.

16. The arrangement of claim 14, wherein the heartrate input tempo, the output device, or both, are integral to or attachable to a juvenile product.

17. The arrangement of claim 14, further comprising an infant-supporting product, wherein the sensory music output selection is audible sound, haptic pulses, or an oscillating motion, and wherein the output device includes an audio speaker facing an infant in the infant-supporting product, a haptic pulsing vibrator positioned adjacent the infant in the infant-supporting product, or a drive device for imparting oscillating motion to the infant-supporting product.

18. The arrangement of claim 14, wherein:
  the heartrate input tempo is a biorhythmic tempo and the input device is an activity tracker or a haptic pulse sensor;
  the heartrate input tempo is a rhythmic tempo of an oscillating motion or a haptic pulse;
  the sensory music output-selection includes audible sounds and the output device includes an audio speaker;
  the sensory music output selection is haptic pulses or an oscillating motion and the output device includes a haptic pulsing vibrator or a drive device for imparting oscillating motion; or
  a combination thereof.

19. The arrangement of claim 14, wherein, in the in-range step, if the adjusted tempo is adjusted to a tempo limit of the permissible tempo range for the sensory music output-selection, and if the heartrate input tempo changes past the tempo limit to outside of the permissible tempo range, then:
  operating the output device to output the sensory music output selection at the tempo limit; or
  transitioning to output a next sensory music output selection having a respective next permissible tempo range spanning the changed heartrate input tempo.

* * * * *